United States Patent [19]

Gregor

[11] 4,163,714

[45] * Aug. 7, 1979

[54] SEPARATING SUBSTANCES WITH PRESSURE-DRIVEN AFFINITY SORPTION MEMBRANES

[76] Inventor: Harry P. Gregor, 150 Lakeview Ave., Leonia, N.J. 07605

[*] Notice: The portion of the term of this patent subsequent to Apr. 30, 1991, has been disclaimed.

[21] Appl. No.: 629,939

[22] Filed: Nov. 7, 1975

[51] Int. Cl.² .................... B01D 13/00; C07G 7/00
[52] U.S. Cl. .................... 210/23 F; 210/500 M; 435/182; 435/815
[58] Field of Search ............. 195/DIG. 11, 63, 4, 195/5, 68; 210/23 F, 500 M

[56] References Cited

U.S. PATENT DOCUMENTS

| | | | |
|---|---|---|---|
| 3,652,761 | 3/1972 | Weetall | 424/12 |
| 3,808,305 | 4/1974 | Gregor | 210/500 M X |
| 3,809,605 | 5/1974 | Schmitt | 195/63 |
| 3,824,150 | 7/1974 | Lilly et al. | 195/63 |
| 3,843,446 | 10/1974 | Vieth et al. | 195/DIG. 11 |
| 4,033,817 | 7/1977 | Gregor | 195/68 X |
| 4,033,822 | 7/1977 | Gregor | 195/68 |

OTHER PUBLICATIONS

"Bound Enzymes Near Commercial Use", from C&EN, Feb. 15, 1971, pp. 86 and 87.

*Primary Examiner*—Frank A. Spear, Jr.
*Attorney, Agent, or Firm*—Sprung, Felfe, Horn, Lynch & Kramer

[57] ABSTRACT

Pressure-driven affinity sorption membranes are prepared from a membrane filter composed of an insoluble matrix polymer or an interpolymer composite and used for separation and purification by passing therethrough solutions containing mixtures, one or more of which forms a specific complex with the ligand on the pore surface of the membrane, washing out the uncoupled solutes, then employing an appropriate displacing or eluting agent to recover the desired component in a pure and concentrated state, all under pressure-driven conditions.

3 Claims, No Drawings

SEPARATING SUBSTANCES WITH PRESSURE-DRIVEN AFFINITY SORPTION MEMBRANES

BACKGROUND OF THE INVENTION

The present invention is directed to the uses in separation of a class of membrane filters to which are attached ligands, substances capable of forming specific complexes with certain species present in a mixture. The specific agents or ligands are attached by chemical bonds to the inner pore surface of the membrane under pressure-driven conditions. The pore diameters of these membranes and their chemical nature are such as to allow for the coupling of a high concentration of these ligands on their inner surfaces, while still providing access to the solute molecules whose separation and purification is desired. These pores must be large enough to allow these soluble substances to be complexed without excessive steric hindrance. Further, the nature of these membranes is such that the excess and undesired components of the mixture can be readily washed out of the membrane under pressure-driven conditions, and then the complex separated and the desired substance displaced in a pure and concentrated state.

This invention teaches new and advantageous means of effecting separations for: analytical purposes; preparative purposes at the laboratory level; purposes of industrial production. It can be compared with the conventional processes of affinity chromatography which are described by several authors, particularly P. Cuatrecasas (J.Biol.Chem., 245, 3059 (1970)). This important technique is employed in biology and medicine and usually involves the use of insoluble gel-type beads of agarose, polyacrylamides or other polymers to which ligands capable of coupling to various molecules in a specific manner are attached. The attachment of ligands may be directly to the gel matrix, but it usually takes place through extended molecular or hydrocarbon chains which place the ligand at varying distances from the gel matrix backbone, the purpose of which is presumably to allow the ligand to come in close proximity to the active site of the molecule being separated. It has been postulated that the ligand must enter the "cleft" of a molecule such as an enzyme, and therefore the chain is a necessary requirement.

These fine beads are employed as specific adsorbents wherein complex mixtures are passed through a bed of such beads and complexes are formed between the ligand and certain molecular species present in the mixture. Then the other, non-coupled solutes present are displaced from the column with water or an appropriate solution in such way that the complex is undisturbed and in this manner a separation of the desired molecular species from the others is achieved. Following this washing procedure the complex is cleaved by passing through the column a soluble ligand as a displacing agent or by a solution of appropriate pH, salt concentration or solute composition, such as the use of urea, guanidine nitrate and the like. All of these techniques are well known in the technical literature.

This classical technique of affinity chromatography has proven to be very useful for the separation of very small amounts of specific substances present in complex mixtures. It has, however, suffered from a number of disadvantages. Among these is the slowness of the procedure and its extremely low capacity. For example, the amount of loading of the ligand on the beads is usually small and usually but a small fraction of the theoretical capacity of the ligand molecules is achieved. Further, since all of these processes are diffusion controlled and the rate of diffusion of proteins (the usual substances being separated) in the pores is very low, the entire procedure of loading can take several hours. The following procedure of washing is similarly quite slow because of the need for high molecular weight impurities to be desorbed and washed out of the bed of beads having fine pore diameters. Following this, the use of a displacement solution can frequently cause a deswelling of the beads and this further retards the rate of elution. Accordingly, the conventional procedures are characterized by a cycle time of many hours or days, and, where the amounts being isolated are of the order of milligrams, the slowness of the procedure results in highly labile molecules being partially or largely decomposed during the periods of the sorption, washing and elution steps.

Conventional affinity chromatography has been applied to the purification of a number of proteins, enzymes and other biologically important molecules. The ligands used include: specific competitive inhibitors; anti-enzymes; enzyme inhibitors. It has been believed by many investigators that it is important that the ligands be fixed at an appropriate and sufficient distance from the gel matrix backbone in order to be capable of binding in a specific manner. However, in more recent years it has been found that the nature of the role of the chain molecule may be more to enhance hydrophobic adsorptive processes in providing for the appropriate distance from the matrix. More recently it has been found that hydrocarbon chains of varying lengths alone can serve as ligands. They do not possess the high degree of selective affinity of enzyme inhibitors, as an example, but they do provide for the separation of related groups or classes of molecules of a biological nature, and these hydrophobic ligands have been employed also for purposes of affinity chromatography.

The teachings of the present invention are directed to novel means for preparing these affinity sorption systems, to the membranes used for these purposes and to a range of applications. These pressure-driven systems can be used for virtually all of the applications in which affinity chromatography gel systems have been used heretofore: they can also be used for high speed separations of an analytical nature, for preparation of materials which are unstable so their isolation must proceed rapidly, and for large-scale separations where a high capacity and high rate of turnover are important.

SUMMARY OF THE INVENTION

In accordance with the present invention, I have found that substantially improved specific ligand systems for purposes of separation and purification can be prepared as follows. First, a reasonably homoporous polymeric matrix membrane of an appropriate porosity (i.e., volume fraction which is pores) and pore diameter is prepared. The specific choice of a specific polymer or polymers, the membrane porosity and pore diameter is determined by the purposes to which the system is to be placed. It is important, further, that the pore surfaces of these membranes contain an appropriately high concentration of ligand groups. Such ligand groups can be provided for by several preparative procedures. First, they can be part of the original matrix polymer or interpolymer mixture used in making the membranes. Or, they can be placed in the pore linings as a result of an appropriate activation-coupling reaction which, when carried out under pressure-driven conditions, has many advantages. Finally, the affinity sorption membrane is used by forcing the mixture to be separated through the membrane pores under appropriate pressure, and when the capacity of the membrane has been filled, the excess solution and solutes are displaced from the membrane by water or an appropriate buffer solution, also under pressure, following which the displacing solution is introduced under pressure to cleave the complexes, displace the molecules desired and concentrate them in the effluent. Following this, the displacing reagent is washed from the membrane and the cycle is repeated.

The membranes of this invention can be prepared in many forms. They can be prepared and used in sheets, supported or unsupported, in the form of tubes, tubelets or hollow fine fibers, in plate-and-frame or wound configurations, and indeed, in any or all of the configurations employed in the field of ultrafiltration membrane technology. The techniques for the preparation of these novel membrane systems are general ones, applicable to a number of different matrix membranes, different ligands, and the separation of a wide range of substances, including those of importance in biology and medicine. One can compare the practical efficiency of this kind of system with those of the conventional gel systems. For example, a 25 ml column containing a typical protein inhibitor of molecular weight 25,000 bound by a chain molecule to the gel can result in the purification of approximately 100 mg of the desired protein in 24 hours. In contrast, a single affinity sorption membrane prepared by the teachings of this invention, one which has a volume of 0.03 ml, can contain about 2 mg of the protein inhibitor and remove in a pure form approximately 1.5 mg of the protein every 15 minutes from a complex mixture. Thus, the relative capacities of the two systems differ by a factor of about 1,000. What I have discovered is a new manner for carrying out affinity sorption processes wherein the usual, slow diffusive steps which invariably control the overall rate of the coupling reaction are eliminated and the long "washout" time similarly eliminated. The new systems of this invention possess a high turnover rate and capacity such that gram or kilogram amounts of material can be separated and purified in short periods of time and with a minimum of decomposition.

DETAILED DESCRIPTION OF THE INVENTION

The present invention is directed to a novel method and to the products produced thereby and to the use of the products produced thereby. It involves the preparation of membrane filters which have a thickness, pore diameter, porosity, configuration, (sheet, fiber, etc.) appropriate to ligands being employed and to the enzyme or the molecule whose separation and purification one desires to effect. This invention, accordingly, can be used in a variety of different systems embodying many different combinations of matrix polymer membranes, ligands, methods of attachment of the ligand to the matrix membrane and substances whose separation and purification is desired. The detailed descriptions which follow apply only to certain of the examples of these systems; the application of the teachings of this invention to other systems will be obvious to one skilled in the art.

The essential components of this invention include: a porous matrix membrane filter of appropriate porosity and structure; a ligand or ligands capable of a specific binding or complexing to other substances present in the mixture to be resolved, such ligands being capable of being attached by chemical bond to the inner pore surfaces of the membrane filter; the treatment of the matrix membrane filter (where such is required) to couple to its inner pore surfaces the specific ligand, usually under pressure-driven conditions; the use of this system under pressure-driven conditions to effect the sorption of the desired substance whose separation and purification is desired; the elution or washing out of the membrane the impurities present in the original mixture; the elution of the desired substance by a displacing agent or other agents capable of breaking the fixed ligand-solute complex; the washing out of the displacing solution; the repetition of this procedure.

The matrix membrane or filter must have properties compatible to its use. It must have pores of a sufficient diameter so that ligands can be attached at a high concentration to the inner pore surfaces, "lining the pores," so to speak. Further, these pores must be of sufficient pore diameter so that the substance being purified can form complexes with the ligands on the inner pore surfaces without steric hindrance. Since many of the substances to be separated are relatively fragile, the pores must be of sufficient diameter so that shear denaturation does not occur during the sorption, washing or elution steps.

This matrix membrane or filter must have sufficient mechanical strength to be capable of being supported mechanically so as to withstand the pressure gradients which are applied across it under conditions of preparation, sorption and other conditions of use.

The specific ligands which can be employed and the chemistry of the processes of attaching these ligands to the pore surfaces of the membranes are not novel, but the manner of the use, namely under pressure-driven conditions, is. Further, it is an important aspect of the present invention not to necessarily require a chain molecule to attach the ligand to the matrix. Thus, the method and means of preparation of the membrane filters are simplified as are the conditions of their use. The method of using the subject of this invention for purposes of separation and purification is taught by this invention, namely that it be carried out under pressure-driven conditions.

Since one of the important advantages of this invention is capacity and speed, it is important that the matrix membranes or filters have a high internal pore surface, which means that they must have a high content of solution, at least 50%, preferably 75 to 90% pore volume. Their pores must be of molecular dimensions, with effective pore diameters at least as large as and not more than about 10 times the diameter of the largest molecule involved, i.e., the complex of ligand with the substance being separated. In general, pore diameters about 3 to 10, especially 3 to 5, times those of the complexes involved are preferred. Thus, the pore diameters generally range from about 15 to 200 AU in diameter. Under these conditions I have found that one achieves the highest capacity of the device, an important consideration in its utility.

While it is recognized that the available means of characterizing pore diameters of membranes of molecular pore dimensions is inadequate, the technique which I have employed for pore diameter determination is that described by Kawabe et al. (J. Colloid & Interface Science 21, 79 (1966)). With this procedure one allows molecules of different sizes to pass through the membrane, and from the relative conductivities, diffusivities or ultrafiltration indices, one can calculate effective average pore diameters. Solute pore diameters are similarly obtained from measurements of transport parameters by methods well known to those skilled in the art.

I have found that the use of the membrane filters of this invention may require that the solutions being treated be free of large colloidal particles of such size that they would act to clog or foul the membrane filters of this invention. I have found that the non-fouling, fixed-charge ultrafiltration membranes described in my U.S. Pat. No. 3,808,305 are particularly useful for the pretreatment of these solutions prior to their separation and purification. The prior ultrafiltration under these conditions acts to remove those colloidal impurities present which can foul the matrix membrane or, by their adsorption in the membrane, can give rise to shear denaturation of fragile ligands or complexed enzymes or proteins within the membrane.

The following examples are provided to more fully illustrate this invention. It will be understood that, because the examples are illustrative, they are not to be construed as limiting the invention, except as defined by the appended claims.

EXAMPLE 1

A matrix membrane was prepared by casting a film from a solution of cellulose acetate (39.4% acetyl groups) in acetone-dimethylformamide mixture (1:3 by weight), forming a membrane onto a glass plate with a conventional doctor blade, allowing the film to evaporate in dry air for 2 minutes, then keeping it in a closed container for 2 hours without loss of solvent, then allowing the membrane to be exposed to water vapor for 30 minutes at 30° C., following which the membrane was rapidly immersed in ice water and washed free of solvent. This membrane was then regenerated to cellulose by conventional hydrolysis in a 9.9 pH buffer for 24 hours at 65° C. to obtain a film having a wet thickness of 25 microns, a water content of 88% and a hydraulic permeability of 3.5 liters per hour at a pressure of 50 psig for an 11.3 cm$^2$ area of film. The film was then treated with cyanogen bromide (40 mg/100 ml) keeping the pH at 11, with this activating solution circulated through the membrane at 50 psig. Following this, all of the excess reagent was washed from the membrane rapidly with water in one minute under pressure-driven conditions (50 psig) and then a solution of 50 mg of trypsin in 100 ml of 0.1 M buffer at pH 6 was pumped through the membrane at 70 psig, the membrane then soaked in this trypsin effluent for 24 hours at 4° C., then washed with distilled water. The final membrane contained 30% of its dry weight as enzyme. It was estimated that the pores of this membrane both before and after coupling were approximately 200 AU in diameter.

The pressure-driven affinity absorption separation of soy bean and pancreatic trypsin inhibitors was then performed. First, a crude mixture containing approximately 100 mg of total protein, of which approximately 15% was soy bean trypsin inhibitor, was dissolved in 50 ml of pH 8.1 buffer. This was passed through the membrane at 50 psig. This required about 10 minutes. This solution then was washed out of the membrane with 20 ml of the same buffer. It was observed that the concentration of protein in the effluent fell rapidly to virtually zero as this volume was passed through, showing that there was virtually no "dead-space" in the membrane. Following this, the tube was eluted with 10 ml aliquots of a solution 6 M in urea and at pH 2 with hydrochloric acid. The sharp absorbance peak in the effluent showed that a protein was being eluted, and after 10 ml of this displacing solution had been passed through, the absorbance again fell to zero showing that all of the complexed molecules, presumably the soy bean inhibitor having a molecular weight of approximately 21,500, had been displaced. From the known absorbance of this protein it was calculated that for every mg of the ligand trypsin originally coupled to the membrane, 0.56 mg of soy bean inhibitor was concentrated and purified. Since one mg of soy bean inhibitor reacts with 1.4 mg of trypsin by weight, it is seen that a nearly stoichiometric ratio of inhibitor to coupled trypsin (about 80%) had been achieved, something quite unexpected in view of the fact that the ligand trypsin had been bound directly to the matrix, without a chain molecule intervening.

Following this, a solution containing about 60 mg/100 ml of protein and with bovine pancreatic trypsin inhibitor having a molecular weight of approximately 6500 present as 5% of this protein was treated. The solution pH was adjusted to 8 and then passed through the same trypsin-coupled membrane. Then the mixture was washed from the membrane with pH 8 buffer, following which the complex was split employing an eluting solution which was 6 M in urea and of pH 2. Immediately a sharp absorbant peak was observed and it was found that the eluted material was at least 90% pure pancreatic trypsin inhibitor. As before, a high yield was observed, with about 0.8 moles of inhibitor recovered per mole of trypsin ligand bound to the membrane.

EXAMPLE 2

The purification of the protein antibody to human serum albumin was achieved as follows: First, a cellulosic membrane was prepared as in Example 1 from a matrix membrane having an average pore diameter of 225 AU, and having 86% of its volume as aqueous solution. This membrane was then activated using cyanogen bromide at pH 11 and at 70 psig and then this was washed out of the membrane in 1 minute. Then a solution of human serum albumin having a concentration of 50 mg of protein in 100 ml of a 0.1 M sodium phosphate buffer at pH 7.4 was passed through at 70 psig. After washing this membrane, the affinity sorption was carried out as follows. A solution containing 50 mg of protein in 100 ml, a crude mixture of which 5% was HSA antibody, was adjusted to pH 7.5 by a phosphate buffer, and then passed through the membrane at a pressure of 20 psig. The effluent absorbance at 280 nm was measured, and a number of effluent samples each 20 ml in volume were collected. The effluent absorbance immediately after the crude mixture was passed through was 0.02. This fell rapidly to 0.001 after some 10 volumes of water were used to displace the crude mixture. Following this, a 2 M sodium chloride solution was passed through the membrane. The absorbance in the tenth volume was 0.001. That in the 11th tube was 0.030, in the 12th it was 0.017, and in the 13th it was 0.001 showing that all of the HSA antibody had been displaced rapidly. From the absorbance measurements it was calculated that the antibody purity was at least 85% of the protein present, compared to that of 5% in the crude mixture. The cycle time was less than 30 minutes for this procedure. The procedure was repeated several times with similar results.

EXAMPLE 3

A membrane was cast from an interpolymer mixture of 2 parts of a 1:1 copolymer of lauroylated styrene and ethylene and 1 part of polyvinylidenefluoride (Kynar, Pennwalt Co.) in a mixture of dichloroethane and dimethylformamide, allowed to dry partially and then coagulated with methanol vapor and finally with water to form a film having pores of 150 AU diameter. The lauroylated styrene-ethylene copolymer was prepared according to the procedures of H. P. Gregor et al. (J.Am. Chem.Soc. 87, 5525 (1965)). The washed film was then used for purposes of affinity sorption using a crude mixture of proteins, and those proteins having a higher degree of hydrophobic bonding were selectively sorbed and then could be eluted. The selectivity of this membrane could be altered by varying the length of the hydrocarbon chain on the acyl chlorie used.

EXAMPLE 4

Carbohydrases can be purified by pressure-driven affinity sorption processes employing the use of a competitive inhibitor as a ligand. A membrane was prepared from a solution of two parts of polyvinylbenzylchloride and one part of polyvinylidenefluoride (Kynar, Pennwalt), cast from a mixture of ethylenechloride-dimethylformamide. This membrane was dried partially and then coagulated by the use of methanol vapor and then by water. Its pore diameters were approximately 350 AU. Then coupling was effected directly to a solution of p-aminophenyl-beta-D-thiogalactopyranoside. This competitive inhibitor forms complexes with a number of carbohydrases including beta galactosidase. A solution containing a mixture of crude *E. coli* beta galactosidase having an activity of 10 units/mg was then passed through the membrane. After cleavage of the complex, the enzyme was recovered with a substantially improved activity of 300 units/mg.

EXAMPLE 5

A pressure-driven affinity sorption system was prepared by dissolving one part of cellulose and one part of polyvinylidinefluoride (Kynar, Pennwalt) in a solution of dimethylsulfoxide-formaldehyde, casting a film therefrom and coagulating it via the vapor phase with water. Following washing with water, the membrane with an average pore diameter of 275 A.U. was then treated with cyanogen bromide at pH 11 in the usual manner under pressure-driven conditions at 50 psig, following which the succinylated 3,3'-diaminodipropylamine derivative of p-aminophenyl-beta-D-thiogalactopyranoside was coupled. Following the coupling of the ligand, the membrane was washed in water at pH 6 and then a crude mixture having an *E. coli* beta galactosidase activity of 2 units/mg was passed through the column, the column was washed and then eluted. The activity of the resulting enzyme was thereby increased to 400 units/mg.

In the foregoing examples as well as generally in the practice of the invention, any superatmospheric pressure can be employed to accelerate the passage through the membrane of activating liquid, ligand and/or of substance to be separated although a pressure of at least about 10 psig, especially about 30 to 120 psig, (except for delicate ligands and/or substances which may be shear-sensitive), gives particularly good results. The pressure or potential, instead of being of a pneumatic or hydraulic type, can be of an electrical nature, i.e. as in the well-known phenomenon of electro-osmosis and/or electrophoresis wherein an electric potential is imposed across a membrane or filter and combinations of the activation-coupling and separation operations effected in that manner. Thus, for example, with trypsin coupled following activation with cyanogen bromide a current which produces a flow of solution through the membrane comparable to that due to a pressure gradient of 70 psi produces a system whose enzymatic activity is nearly the same as one prepared under 70 psi.

It will be appreciated that the instant specification and claims are set forth by way of illustration and not limitation, and that various modifications and changes may be made without departing from the spirit and scope of the present invention.

What is claimed is:

1. A process which comprises forcing a solution of a ligand through a homoporous homogeneous ultrafiltration membrane under a pressure equivalent to at least about 10 psig, said membrane having an average pore size of about 15 to 200 Angstroms in diameter and being receptive to coupling said ligand, removing excess liquid, forcing through said ligand-coupled membrane under a pressure equivalent to at least about 10 psig a solution of a mixture of substances of which at least one substance but not all has an affinity for said ligand whereby said one substance is selectively extracted from said mixture and held as a complex by said ligand, said membrane having pores averaging in size from about 3 to 10 times the diameter of the ligand-substance complex.

2. The process of claim 1, wherein the membrane is rendered receptive to said ligand by forcing an activating agent through said membrane under a pressure equivalent to about 70 to 120 psig, and the ligand is thereafter forced through said membrane under a pressure equivalent to about 30 to 120 psig.

3. The process of claim 2 wherein said membrane is cellulosic, said activating agent is cyanogen bromide and said ligand is trypsin.

* * * * *